United States Patent [19]

Merkl

[11] 4,116,85

[45] Sep. 26, 197

[54] METHOD OF PREPARING OXYGEN-CONTAINING BLEACH AND PRODUCT SO PRODUCED

[76] Inventor: George G. Merkl, 46 Sunset Ct., Haworth, N.J. 07651

[21] Appl. No.: 758,343

[22] Filed: Jan. 10, 1977

Related U.S. Application Data

[63] Continuation-in-part of Ser. No. 534,084, Dec. 23, 1974, abandoned.

[51] Int. Cl.[2] .................. C07C 179/20; C07C 179/02; C11D 3/395; C11D 7/54

[52] U.S. Cl. ........................................ 252/186; 8/111; 252/95; 260/610 R; 260/610 A; 423/273; 423/582

[58] Field of Search ...................... 252/186, 95; 8/111; 423/272, 273, 582; 260/610 R, 610 A

[56] References Cited

U.S. PATENT DOCUMENTS 3,413,089 11/1968 Coussemont et al. ............... 423/58

OTHER PUBLICATIONS

Condensed Chemical Dictionary, 6th Ed., 1961, p. 57

*Primary Examiner*—Benjamin R. Padgett
*Assistant Examiner*—Irwin Gluck

[57] ABSTRACT

Oxygen-containing bleach products are prepared b reaction of a source of hydroperoxy groups, such a hydrogen peroxide or ozone, with a water-soluble mul ti-metal, inorganic, amide group-containing monomeri complex. Such complex is obtained by reacting, in th presence of aqueous ammonia, at least one non-alkalin metal with an alkali metal hydroxide in accordanc with a reaction sequence which produces reactive NH groups.

9 Claims, 10 Drawing Figures

METHOD OF PREPARING OXYGEN-CONTAINING BLEACH AND PRODUCT SO PRODUCED

RELATED APPLICATION

This application is a continuation-in-part of applicant's co-pending application Ser. No. 534,084, filed on Dec. 23, 1974, now abandoned and entitled "Soaps and Detergents".

SUMMARY OF THE INVENTION

The present invention is directed to the production of heretofore unknown oxygen-containing bleach products, specifically bleach products obtained by reaction of hydrogen peroxide or ozone with a multi-metal, water-soluble, inorganic amide group ($NH_2$)-containing monomeric complex.

Co-pending application Ser. No. 631,949, filed on Nov. 17, 1975, now U.S. Pat. No. 4,029,747, issued June 14, 1977 discloses a method for producing certain novel inorganic monomeric and polymeric complexes and such complexes so produced. In accordance with the present invention, novel oxygen-containing bleach products are prepared by reaction of the monomeric complex, with a source of hydroperoxy groups, specifically an inorganic source of hydroperoxy groups, such as hydrogen peroxide or ozone.

It is theorized from analytical data that each monomeric unit of the monomeric complexes employed to produce the oxygen-containing bleach products includes a plurality of reactive $NH_2$ groups. When such monomeric complexes are reacted with a source of hydroperoxy groups, such as hydrogen peroxide, the hydroperoxy groups replace and/or chemically combine with the $NH_2$ groups to produce a final product containing hydroperoxy groups. This final bleach product is formed in a solid, particulate form, which is water-soluble, although water solubility decreases with increasing hydroperoxy group content on the non-alkaline metal.

The reaction between the source of hydroperoxy groups and multi-metal, water-soluble, inorganic amide group-containing monomeric complexes is carried out by simply contacting the reactants while maintaining the reaction temperature below about 75° F., to insure the stability of the final bleach product. Since the reaction is exothermic, cooling may be required. Preferably, cooling is provided to maintain the reaction temperature at room temperature or below.

In preparing the bleach products of the present invention, it is preferable to minimize the water content of the reaction system. To achieve this, more concentrated reactants are preferably utilized. A minimum amount of water will allow the formation of a solid particulate product by mixing the source of hydroperoxy groups and monomeric complex.

The oxygen-containing bleach of the present invention can be effectively utilized as an industrial or household bleach. The bleach releases active oxygen in an aqueous environment and this active oxygen is responsible for the active bleach properties. Since effective bleaching is achieved without chlorine or other halogen, a safer, nonpolluting, more efficient product is provided.

DESCRIPTION OF THE PREFERRED EMBODIMENTS

Figure 1:
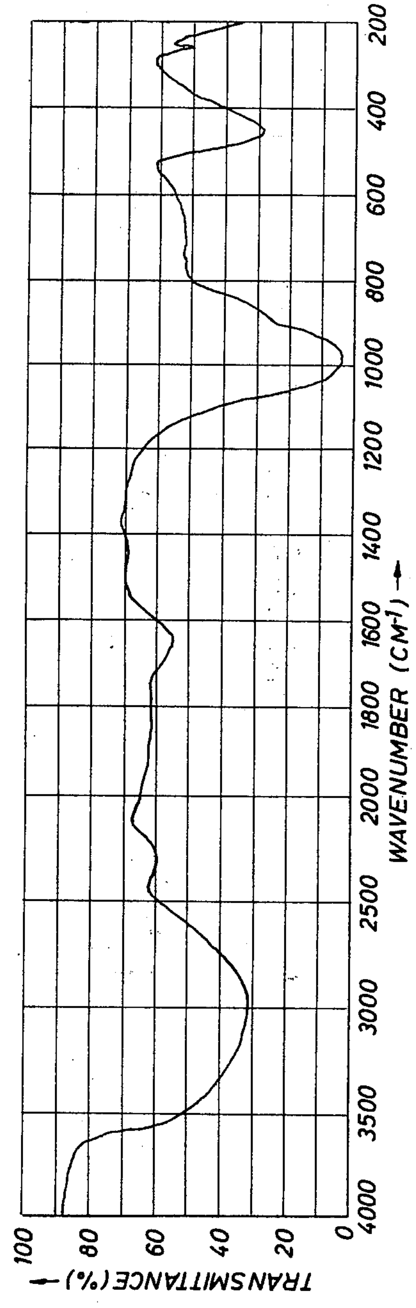
FIG. 1 is an infra-red scan of a monomeric complex reactant containing sodium and silicon metals.

The oxygen-containing bleach products in accordance with the present invention are prepared by contacting and reacting a source of hydroperoxy groups, specifically an inorganic source of hydroperoxy groups, such as hydrogen peroxide or ozone, with a water-soluble, multi-metal, inorganic, amide group-containing monomeric complex. The oxygen-containing bleach is prepared as a solid particulate bleach product which releases active oxygen in an aqueous environment. This provides for the effective bleaching characteristics of this product. Generally, the bleach product which is prepared is water-soluble, although water solubility decreases with increasing hydroperoxy group content specifically as the hydroperoxy groups are attached to the non-alkaline metal. It is theorized in accordance with the present invention that the $NH_2$ groups of the inorganic monomeric complex are replaced by hydroperoxy groups ($HO_2$) through the reaction of the present invention. The released $NH_2$ groups pick up hydrogen ions an can be observed as ammonia evolved from the reaction. Since the monomeric complexes utilized as reactants contain a plurality of $NH_2$ groups, this replacement can be carried out so that all or a portion of $NH_2$ groups are replaced with hydroperoxy groups.

To prepare the oxygen-containing bleach products of the present invention, the following reactants are required:

A. Water-soluble, multi-metal, inorganic, amide group-containing monomeric complex; and B. A source of hydroperoxy groups, specifically hydrogen peroxide, or ozone.

These reactants are individually discussed below.

The Monomeric Complex

A full description of the preparation of the monomeric complex reactants utilized in the process of the present invention can be found in applicant's co-pending application Ser. No. 631,949, filed on Nov. 17, 1975, the disclosure of which is herein incorporated by reference.

In general, the monomeric complex reactants are prepared in accordance with a reaction sequence which involves: introducing an excess of a non-alkaline metal or metals into a reaction vessel, preferably already containing aqueous ammonia, and thereafter incrementally adding an alkali metal hydroxide in such manner as to create localized areas of high alkali concentration, the pH approaching a value of 14 in such localized areas. The hydroxide in these areas of high concentration, in combination with the reactive $NH_2$ groups provided by the aqueous ammonia, causes dissolution of the non-alkaline metal, the formation of non-alkaline metal ions and the production of a monomeric complex reactant as employed in accordance with the present invention. Accordingly, the reactants necessary to produce such monomeric complex include at least one non-alkaline metal, a source of $NH_2$ groups, particularly aqueous ammonia, and an alkali metal hydroxide. These reactants will be individually discussed below.

The non-alkaline reactant is broadly selected from those non-alkaline metals of Groups I-VIII of the Periodic Table. Representative, non-limiting examples of applicable non-alkaline metals include:

Group I-B: copper, silver, gold
Group II-A: beryllium, magnesium
Group II-B: zinc, cadmium
Group III-A: aluminum, gallium, indium
Group IV-A: silicon, tin, lead
Group IV-B: titanium, zirconium, hafnium
Group V-A: antimony, bismuth
Group V-B: vanadium, niobium, tantalum
Group VI-A: chromium, molybdenum, tungsten
Group VI-B: manganese
Group VIII: iron, cobalt, nickel palladium, rhodium It should be recognized that while silicon, as a member of Group IV–A, is not generally defined as a metallic element, silicon acts as a non-alkaline metal in preparing the monomeric complex reactant. Accordingly, the expression "non-alkaline metal of Groups I–VIII of the Periodic Table" is meant to embrace any and all of the above and equivalent metals, including silicon. As will be further recognized, the term "non-alkaline metal of Groups I–VIII of the Periodic Table" does not embrace the alkali metals of Group I–A. The alkaline earth metals, calcium, strontium, and barium of Group II–A, are similarly not within the scope of the term. On the other hand, beryllium and magnesium of Group II–A can be applicably employed in the preparation of the monomeric complex reactant and these metals also fall within the scope of the expression "non-alkaline metal of Groups I–VIII of the Periodic Table.

While any of the above non-alkaline metals can be utilized to form the monomeric complex reactant which is contacted and reacted with the source of hydroperoxy groups to form the oxygen-containing bleach in accordance with the present invention, the non-alkaline metal utilized is preferably one which contributes additional valuable properties to the bleach product, particularly those metals which have heretofore been used in preparation of industrial bleaches, soaps, etc. Preferred examples of such metals include magnesium, aluminum, silicon, zinc, titanium, zirconium, molybdenum, and tungsten. While these metals are preferred and while the representative exemplification will be directed primarily thereto, it should be recognized from applicant's co-pending application Ser. No. 631,949 that the monomeric complex reactant can be formed from any of the non-alkaline metals of Groups I–VIII of the Periodic Table, and accordingly, the oxygen-containing bleach product of the present invention can be effectively prepared from any such monomeric complexes.

An alkali metal hydroxide is utilized as the second reactant to produce the monomeric complex reactant. This reactant can comprise any hydroxide of a metal of Group I–A of the Periodic Table, principally, sodium hydroxide, potassium hydroxide or lithium hydroxide.

The alkali metal hydroxide, specifically sodium hydroxide or potassium hydroxide, dissolves in the aqueous medium in the monomeric complex production reaction. The alkali metal hydroxide can be employed either in solid form or in the form of a prepared aqueous solution of the alkali metal hydroxide. In solid form, the alkali metal hydroxide can be conveniently in the form of pellets, powder or flakes.

Analytical studies have shown that the inorganic monomeric complexes useful in accordance with the present invention contain $NH_2$ groups. Accordingly, the third essential reactant in the method of producing the monomeric complexes comprises any substance which, under the conditions of the reaction, acts as a source of reactive $NH_2$ groups.

In the preferred reaction for preparation of the monomeric complex reactant, the source of $NH_2$ groups comprises aqueous ammonia. $NH_2$ groups are liberated when this aqueous ammonia is brought into reactive contact with the alkali metal hydroxide and non-alkaline metal. As an alternative, ammonia gas may be used, introducing the gas into the reaction system by any suitable conventional techniques, such as bubbling. The use of ammonia gas in this manner also permits a supplementing of the supply of the $NH_2$ source at any stage during the reaction.

Another applicable alternative $NH_2$ source may be formed directly in the reaction medium by utilizing as a reactant an $NO_x$ gas, i.e., NO and/or $NO_2$, or nitric acid. The use of $NO_x$ gas or nitric acid as a source of reactive $NH_2$ groups appears applicable due to the dissolution of the non-alkaline metal and concurrent hydrogen ion production. These hydrogen ions react with the $NO_x$ groups in the reaction medium, creating in situ the reactive $NH_2$ groups. These reactive $NH_2$ groups are then available for metal amide formation and formation of the inorganic monomeric complex reactant. When the non-alkaline metal is not easily dissolved in the reaction medium upon alkali metal hydroxide addition, it may be necessary to assist the dissolution so as to develop the hydrogen ions necessary for reactive $NH_2$ group production. This can be achieved, for example, by supplementing the $NO_x$ or nitric acid with ammonia gas at the onset of the reaction.

As disclosed in applicant's co-pending application Ser. No. 631,949, filed Nov. 17, 1975, the reaction between the non-alkaline metal, alkali metal hydroxide and source on $NH_2$ groups proceeds through a first endothermic phase wherein a monomeric complex is produced and thereafter, through an exothermic phase wherein the monomeric complex polymerizes into a polymeric complex form. It is presumed from analytical data which has been obtained that, during this polymerization stage, a substantial portion of the $NH_2$ groups of the inorganic monomeric complex are broken up into NH and hydride groups which are present in the polymerized complex. It has been determined in accordance with the present invention, however, that an effective bleach product cannot be obtained through the reaction of the source of hydroperoxy groups and inorganic polymeric complex, presumably due to the lack of a substantial number of reactive $NH_2$ groups in the polymerized complex and the difficulty of the hydroperoxy groups to replace or chemically combine with the NH or hydride groups. Accordingly, the process of the present invention for the preparation of the oxygen-containing bleach product requires the use of the monomeric complex.

As described in applicant's co-pending application Ser. No. 631,949, filed Nov. 17, 1975, after an endothermic phase of reaction in which the monomeric complex is formed, a natural exothermic phase is entered. In order to produce the monomeric complexes useful as reactants in the process of the present invention, however, such exothermic phase must not be allowed to go to completion since, as indicated previously, the polymeric complexes cannot be effectively used in producing the oxygen-containing bleach products. Generally, however, the reaction for preparing the monomeric complexes is allowed to go slightly into the exothermic phase, for example, up to a temperature of about 140° F., in order to rid the monomeric complex formed of any free ammonia. At this temperature, there may be some slight polymerization of the monomeric complex and some slight splitting of the $NH_2$ groups into NH and hydride groups; however, this slight degree of polymerization will not interfere with the basic function of the monomeric complex reactant in the preparation of the oxygen-containing bleach of the present invention. Furthermore, where substantial polymerization does occur, the reaction can be driven back to its monomeric stage by the simple addition of ammonia. Accordingly, the expression "water-soluble multi-metal inorganic amide group-containing monomeric complex" as used throughout is meant to embrace the above-discussed complex, possibly including a minor amount of polymerized complex.

Throughout the foregoing and following description, reference has been made to the production of an inorganic monomeric "complex". The term "complex" is used because the structural configurations of these products have not been precisely determined. However, extensive analysis has been conducted which has established the monomeric nature of the products and the presence of certain functional groups. In view of the difficulty in precisely determining the structural configuration of products obtained through complex chemical reactions, the expression "complex" is deemed aptly descriptive of this reactant used in the method of the present invention.

The Source of Hydroperoxy Groups

The second essential component in preparing the oxygen-containing bleach of the present invention is a source of hydroperoxy groups. In this regard, the present invention can employ any source of hydroperoxy groups effective to introduce hydroperoxy groups into the backbone of the monomeric complex. Such source of hydroperoxy groups is preferably hydrogen peroxide or ozone, most preferably an aqueous solution of hydrogen peroxide. As will be appreciated from the discussion hereinafter involving the reaction parameters, when employing an aqueous solution of hydrogen peroxide, the concentration of the hydrogen peroxide should be as high as possible in order to minimize the amount of water present in the reaction system. In this way, it is possible to effectively produce the oxygen-containing bleach product as a substantially dry powder. Of course, in lieu of an aqueous solution of hydrogen peroxide, 100% hydrogen peroxide can be employed in the process of the present invention; however, highly concentrated hydrogen peroxide must be handled very carefully.

When utilizing ozone, for example, as the source of hydroperoxy groups, the ozone can be bubbled into the reaction system containing the aqueous solution of the inorganic monomeric complex. Reaction between an aqueous solution of hydrogen peroxide and the aqueous solution of the inorganic monomeric complex can be effectively achieved simply by mixing these components in a suitable vessel.

Reaction Parameters

As indicated above, when employing the preferred form of the source of hydroperoxy groups, it is merely necessary to contact, through mixing, the aqueous solution of the inorganic monomeric complex and hydrogen peroxide or aqueous solution thereof while maintaining the reaction temperature below about 75° F. This provides sufficient contact between the hydrogen peroxide and monomeric complex such that the hydroperoxy groups of the hydrogen peroxide replace and/or chemically combine with the amide groups of the inorganic monomeric complex to produce a final bleach product containing hydroperoxy groups. Such bleach product containing hydroperoxy groups crystallizes out of the reaction system during the mixing of the reactants.

The oxygen-containing bleach product which is formed as a crystalline solid redissolves in the aqueous medium from which it is formed if the product is not immediately removed from the reaction medium. With increasing hydroperoxy group content i.e., as the hydroperoxy groups replace an increasing member of the $NH_2$ groups attached to the non-alkaline metal of the multi-metal complex, this bleach product has decreasing solubility. However, due to the solubility in the aqueous medium it is preferred in accordance with the present invention to limit the amount of water present in the reaction system, and by so doing, directly form the oxygen-containing bleach product as a substantially dry solid product, specifically a substantially dry powder. For this reason, concentrated hydrogen peroxide solutions are preferred over dilute hydrogen peroxide solutions. In addition, the water content of the inorganic monomeric complex solution can be reduced prior to reaction by evaporating some of the water present. Preferably, after preparation of the inorganic monomeric complex and removal of excess unreacted non-alkaline metal, the aqueous solution of the inorganic monomeric complex is heated to evaporate about one-half of its water content. This concentrated inorganic monomer solution is then very effective for producing the oxygen-containing bleach product in the form of a substantially dry powder.

The selection of an appropriate water content for a particular system can be easily carried out by one skilled in the art through routine experimentation. It is merely important that the water not be present in such an excess amount that after production of the oxygen-containing bleack product, the solid redissolves in the aqueous medium. The selection of a water content to achieve a dry product or a substantially dry product through the mixing of the aqueous solution of the inorganic monomeric complex and hydrogen peroxide can be very easily done. Precise selection of the water content is not necessary since if a wet product is formed, drying can be achieved by vacuum evaporation or simply by gently heating the wet solid. Care should be taken to avoid temperature in excess of about 160° F. since temperatures in excess of this value tend to degrade the oxygen-containing bleach.

As indicated previously, it is theorized that the inorganic monomeric complex utilized as a reactant in accordance with the present invention contains a plurality of $NH_2$ groups, this number generally corresponding to the total valence of the alkali metal and non-alkaline metal. The reaction of such inorganic monomeric complex with the source of hydroperoxy groups, specifically hydrogen peroxide, can be effectively carried out in order to replace and/or chemically combine with one or more of such $NH_2$ groups in order to produce the final oxygen-containing bleach product. The degree of replacement and/or chemical combination will depend upon the molar ratio of the inorganic monomeric complex to the hydrogen peroxide. This molar ratio can suitably vary from 1:1 or below to 5:1 or more. Again, the particular molar ratio of the hydrogen peroxide to the inorganic monomeric complex can be easily selected by one skilled in the art depending upon the final hydroperoxy content desired in the oxygen-containing bleach product.

The preparation of the oxygen-containing bleach product can be achieved by merely contacting, through mixing, the above-described reactants in a suitable vessel under ambient temperature and pressure conditions. Preferably, the contacting is carried out at a temperature of room temperature or below. Since the reaction between the inorganic monomeric complex and hydrogen peroxide or other equivalent source of hydroperoxy groups is exothermic, it may be necessary to cool the reaction vessel, through any suitable means. The reaction medium should not be allowed to go higher than 100°-105° F. since at temperatures above this range it becomes extremely difficult to control the reaction as the exothermic reaction becomes great and a breakdown of the oxygen-containing bleach product is substantial. The use of an ice bath to effectively maintain the temperature below this value, preferably at room temperature or below, can be easily carried out.

The present invention will now be described by reference to the following specific examples. Such examples are presented for purposes of illustration only and the present invention cannot under any circumstances be deemed limited thereto. In these following examples, unless otherwise stated, all parts and percentages are by weight.

EXAMPLE 1

A silicon-sodium monomeric complex is prepared following the reaction sequence and parameters described in co-pending application Ser. No. 631,949, filed on Nov. 17, 1975. The reactants include 616 g of silicon metal, 1,925 g of aqueous ammonia (28° Be) and 440 g of sodium hydroxide, the latter being metered slowly into the reaction system in order to develop an endothermic phase of reaction. After completion of the reaction, 320 g of silicon are removed from the reaction system. Accordingly, some 296 g of silicon enter into the inorganic monomeric complex. The complex is diluted with 500 ml of deionized water. The aqueous solution of the monomeric complex has a specific gravity of 1.461.

To prepare the oxygen-containing bleach product of the present invention, some 50 ml of this aqueous solution of the silicon-sodium monomeric complex are reacted with 8 ml of hydrogen peroxide (50%) by simply mixing the reactants under ambient temperature and pressure. This mixing results in the formation of a white, substantially dry powder. During the mixing of the hydrogen peroxide with the silicon-sodium monomeric complex, the release of ammonia from the monomeric complex is detected.

Figure 2:
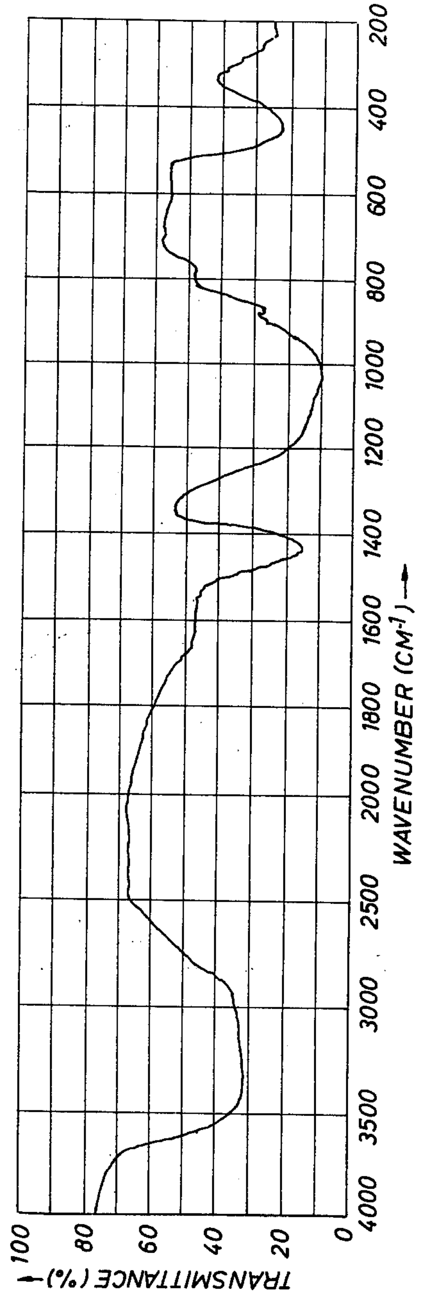
FIG. 2 is an infra-red scan of an oxygen-containing bleach product in accordance with the present invention, formed by reacting the silicon-sodium monomeric complex of FIG. 1 with hydrogen peroxide.

FIG. 1 represents an infra-red scan of a silicon-sodium monomeric complex produced as described above. FIG. 2 represents an infra-red scan of the silicon-sodium bleach prepared as described above by reaction of the silicon-sodium monomeric complex with hydrogen peroxide. By comparing FIGS. 1 and 2, an increased hydroperoxy group content in the bleach product can be observed. In this regard, the hydroperoxy group comes out at approximately 875 $cm^{-1}$ and at about 2,500 $cm^{-1}$. Due to the water present in the system, some of the amide group which can be observed at 1,600 $cm^{-1}$ are covered with hydroxy. In addition, the spectrum for silicon bonding partially covers some of the spectrum where the amide and hydroperoxy groups would be observed. Oxygen bonding also appears at 875 $cm^{-1}$.

EXAMPLE 2

Following the procedure of Example 1, a bleach-containing molybdenum metal is prepared.

First, a molybdenum-sodium monomeric complex is prepared by reacting molybdenum metal (4,538.8 g) in aqueous ammonia (1,930.6 g-28° Be) with the controlled incremental addition of 630.4 g of sodium hydroxide. After the addition of the sodium hydroxide the reaction system is heated slightly to 85°-100° C., utilizing a dry ice condenser to prevent ammonia escape. Due to the slow reaction of molybdenum, this slight heating is necessary in order to initiate the dissolution of the molybdenum in the reaction system. The reaction is run in this manner for several days after which a low heat of approximately 30° C. is applied. The reaction thereafter continues for approximately one week without any heat in order to prepare the final molybdenum-sodium monomeric complex. The final product has a specific gravity of 1.332.

To prepare the molybdenum-containing bleach, 50 ml of the above monomeric complex are reacted with 5 ml of hydrogen peroxide. This reaction is extremely exothermic. The reaction occurs merely by mixing the monomeric complex and aqueous hydrogen peroxide.

Figure 3:
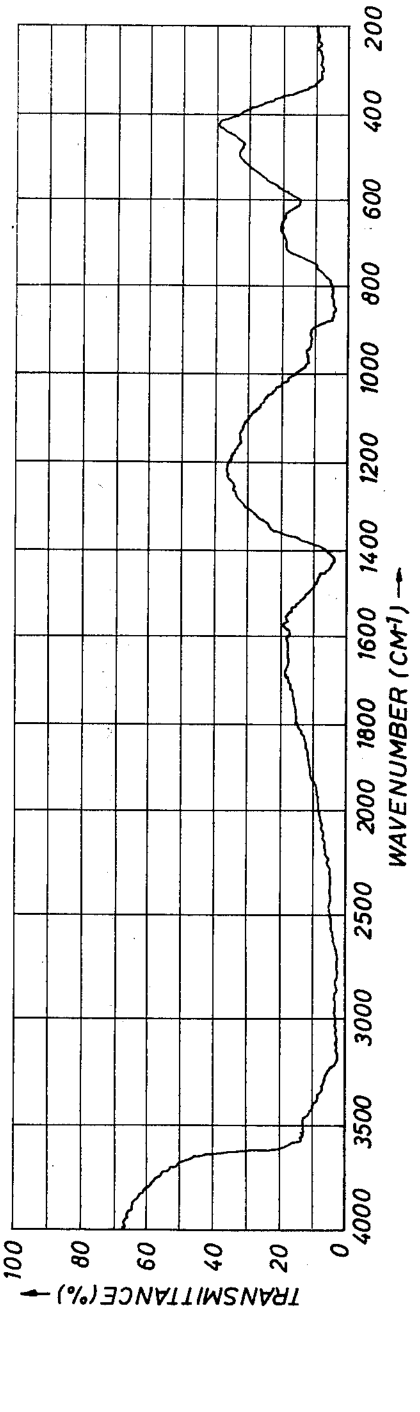
FIG. 3 is an infra-red scan of a monomeric complex reactant containing sodium and molybdenum metals.
Figure 4:
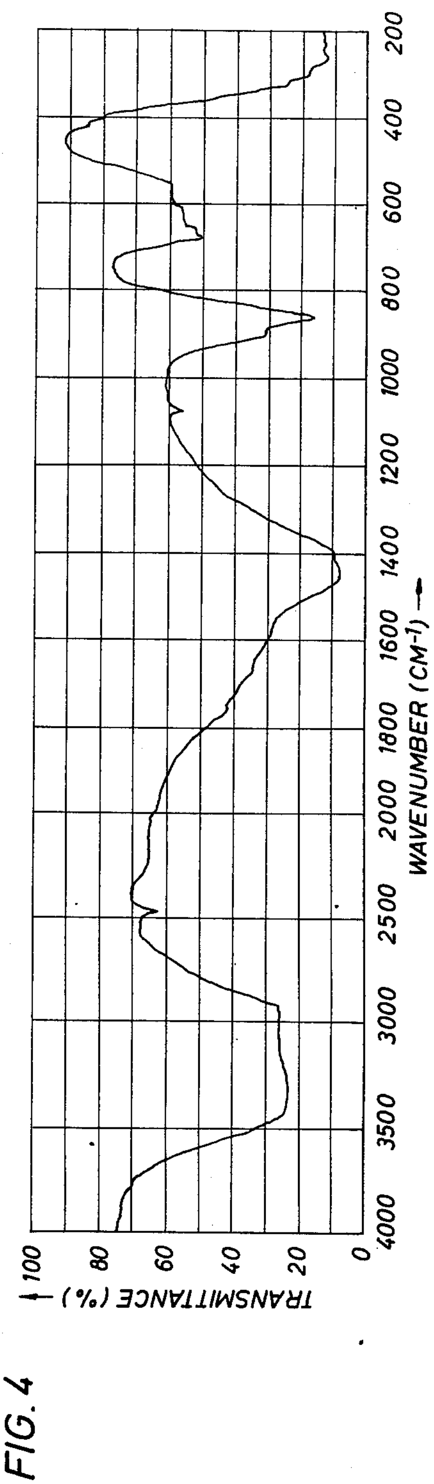
FIG. 4 is an infra-red scan of an oxygen-containing bleach product in accordance with the present invention formed by reacting the molybdenum-sodium monomeric complex of FIG. 3 with hydrogen peroxide.

FIG. 3 is an infra-red scan of a molybdenum-sodium inorganic monomeric complex prepared as above. FIG. 4 is an infra-red scan of a molybdenum-containing bleach prepared by reacting the molybdenum-sodium inorganic monomeric complex with hydrogen peroxide. Noting FIG. 4, the peaks at approximately 875 $cm^{-1}$ and 2,500 $cm^{-1}$ identify the presence of hydroperoxy groups within the bleach product. Also, a comparison of FIG. 3 and 4 shows some decrease in the amide group content in the bleach when compared with the starting monomeric complex.

EXAMPLE 3

In this example an aluminum-containing bleach is prepared by following the procedure, substantially as described in connection with Example 1.

To prepare the aluminum-containing monomeric complex, 713 g of aluminum are introduced into 1,820 g of aqueous ammonia (28° Be) and thereafter, 520 g of sodium hydroxide pellets are incrementally introduced into the reaction system over a period of about two hours. The reaction system develops a natural endothermic phase and thereafter begins to enter an exothermic phase. The reaction is terminated by withdrawing unreacted aluminum when the temperature of the reaction system reaches 150° F. Some 647 g of aluminum are removed from the reaction system, indicating that 66 g of aluminum are introduced into the monomeric complex. The monomeric complex obtained has a specific gravity of 1.314.

To prepare the aluminum-containing bleach, 50 ml of the above-prepared monomeric complex are reacted with 8.33 ml hydrogen peroxide, the components being mixed thoroughly until the bleach crystallizes as a substantially dry powder. The formation of the bleach by mixing the aluminum-containing monomeric complex and hydrogen peroxide is exothermic.

Figure 5:
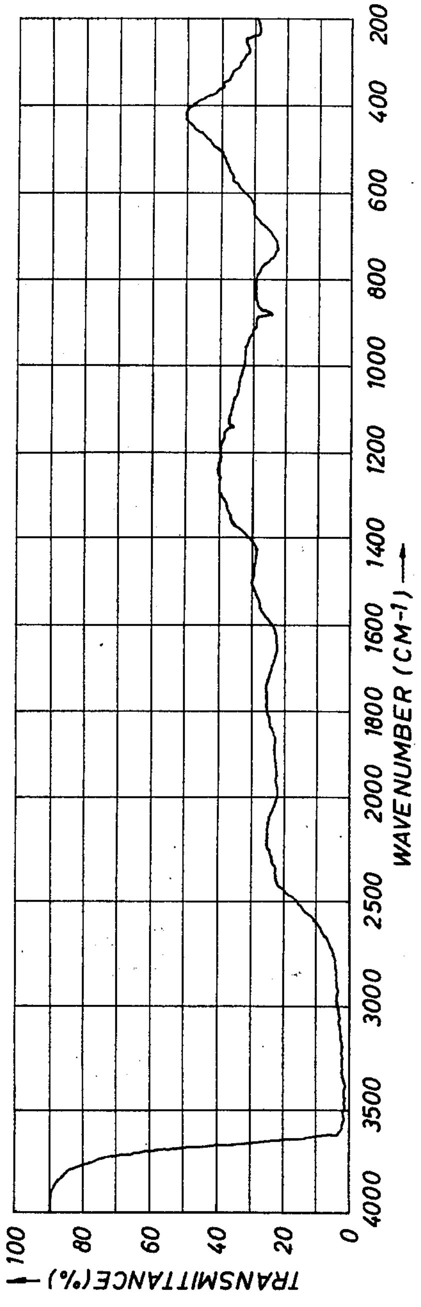
FIG. 5 is an infra-red scan of a monomeric complex reactant containing aluminum and sodium metals.
Figure 6:
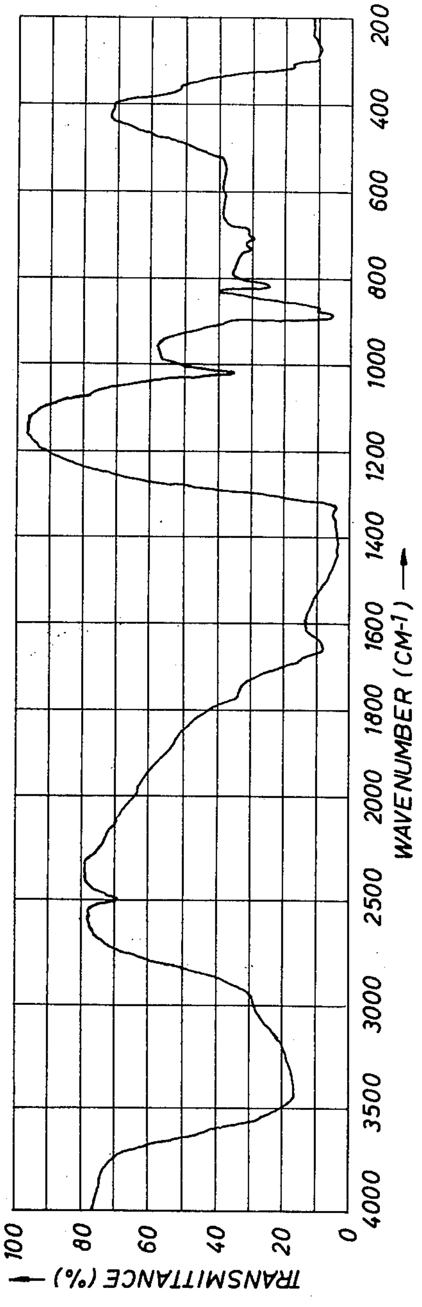
FIG. 6 is an infra-red scan of an oxygen-containing bleach product in accordance with the present invention formed by reaction of the aluminum-sodium monomeric complex of FIG. 5 with hydrogen peroxide.

FIG. 5 is an infra-red scan of an aluminum-sodium monomeric complex prepared in accordance with the procedure above; and FIG. 6 is an infra-red scan of an aluminum-containing bleach obtained by mixing such a monomeric complex with hydrogen peroxide. Reference to FIG. 6 will again reveal the presence of the hydroperoxy groups in the bleach product and a comparison of FIGS. 5 and 6 illustrates the apparent reduction in the amide group content of the monomeric complex when converted to bleach.

EXAMPLE 4

Following the procedure of Example 1, the zirconium-containing oxygen-containing bleach is prepared from a zirconium-sodium inorganic monomeric complex. This complex is prepared through a reaction which involves introducing 2,241.6 g of zirconium metal into 1,078 g of aqueous ammonia (28° Be) and thereafter incrementally introducing 246.4 g of sodium hydroxide pellets. The feed of sodium hydroxide is accomplished by approximately one hour and forty minutes, and thereafter, the reactants are maintained undisturbed, while entering an endothermic phase of reaction. The reaction is terminated by removing unreacted zirconium metal, the monomeric complex having a specific gravity of 1.227. To prepare the bleach product, 50 ml of this zirconium-containing monomeric complex are mixed with 10 ml of hydrogen peroxide (50%), the mixing being caried out thoroughly until crystallization of the bleach occurs. This mixing results in a slightly exothermic reaction. The hydroperoxy group content of the bleach is found to be 16.66%.

Figure 7:
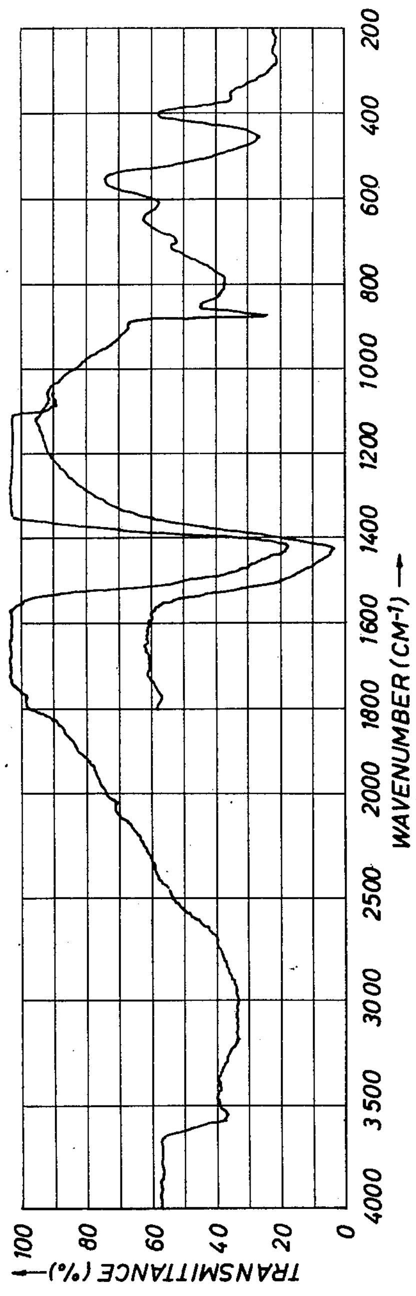
FIG. 7 is an infra-red scan of a monomeric complex reactant containing zirconium and sodium metals.
Figure 8:
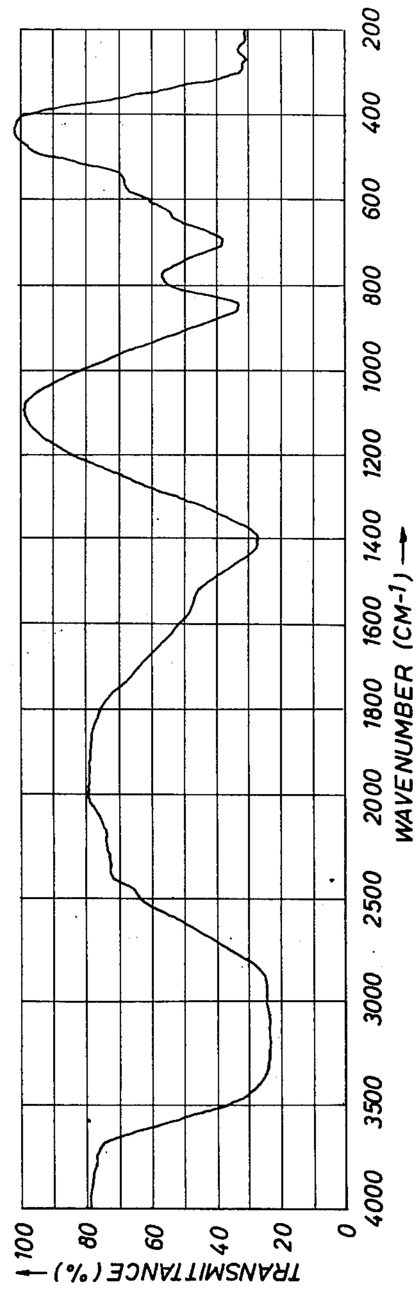
FIG. 8 is an infra-red scan of an oxygen-containg bleach in accordance with the present invention formed by reacting the zirconium-sodium monomeric complex of FIG. 7 with hydrogen peroxide.

FIG. 7 represents an infra-red scan of a zirconium-containing monomeric complex produced as described above; FIG. 8 represents the infra-red scan of a bleach obtained by reacting such a zirconium-sodium monomeric complex with hydrogen peroxide. Again, it can be seen that the bleach has an increased hydroperoxy group content, as exemplified by the small peak at about 2,500 $cm^{-1}$ in FIG. 8 and the increased size of the peak at about 875 $cm^{-1}$.

EXAMPLE 5

Following the procedure of Example 1, a titanium-sodium monomeric complex is prepared and is subsequently utilized to prepare a titanium-containing bleach. The titanium monomer is prepared by reacting 1,997.52 g of titanium metal in 2,080.75 g of aqueous ammonia (28° Be) with 951.2 g of sodium hydroxide pellets, introduced incrementally. The sodium hydroxide is fed over a time period of approximately 40 minutes after which the reactants are allowed to remain undisturbed in the reaction vessel. The reaction is terminated by withdrawing unreacted titanium from the reaction system, yielding a monomeric complex having a specific gravity of 1.432.

This monomeric complex is reacted with hydrogen peroxide by mixing 50 ml of a monomeric complex with 5 ml of a 50% hydrogen peroxide solution. The components are mixed thoroughly until the bleach product crystallizes as a substantially dry powder. The reaction between the monomeric complex and hydrogen peroxide is mildly exothermic. The hydroperoxy group content of the final bleach is found to be approximately 9%.

Figure 9:
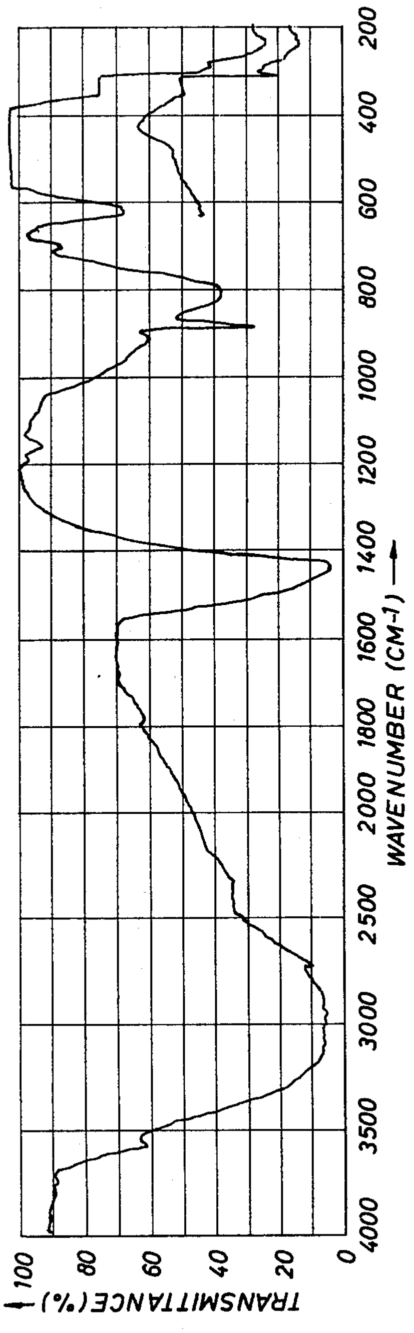
FIG. 9 is an infra-red scan of a monomeric complex reactant containing titanium and sodium metals.
Figure 10:
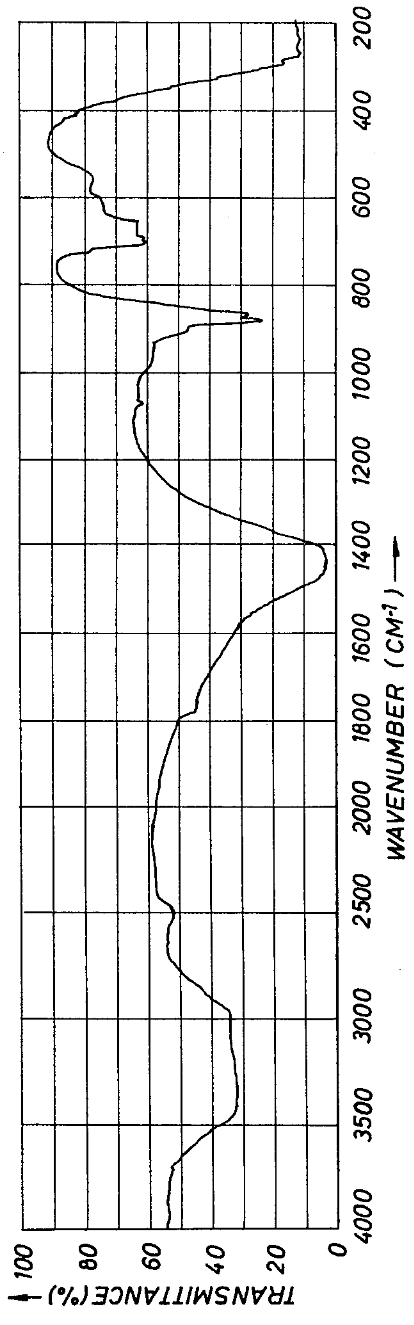
FIG. 10 is an infra-red scan of an oxygen-containing bleach in accordance with the present invention formed by reacting the titanium-sodium monomeric complex of FIG. 9 with hydrogen peroxide.

FIG. 9 represents an infra-red scan for the titanium-sodium monomeric complex prepared as above. FIG. 10 represents an infra-red scan for a titanium-containing bleach obtained by reacting such titanium-sodium inorganic monomeric complex with hydrogen peroxide. It can again by seen by comparing FIGS. 9 and 10 that there is an increase in the hydroperoxy group content in the bleach, as evidenced by the increased peak at about 875 $cm^{-1}$ and the peak at approximately 2,500 $cm^{-1}$.

EXAMPLE 6

Following a procedure similar to that of Example 1, a tungsten-sodium monomeric complex is produced by reacting 603.5 g of tungsten in 245 g of aqueous ammonia (28° Be) through the incremental addition of 40 g of sodium hydroxide pellets. The sodium hydroxide pellets are introduced over a time period of approximately one and one-half hours. After introduction of the sodium hydroxide, the reaction is pushed by utilizing a 1.5 amp current in order to accelerate the dissolution of the tungsten metal.

After allowing the reaction to remain in this manner for a period of time, the reaction is terminated by withdrawal of unreacted tungsten. The monomeric complex has a density of 1.230. A bleach product containing tungsten is prepared by reacting 20 ml of this monomeric complex with 4.5 ml of hydrogen peroxide (50%).

EXAMPLE 7

Utilizing a similar procedure as that described above, a magnesium-containing bleach is prepared from a magnesium-sodium monomeric complex. The complex is prepared by reacting 432 g of magnesium metal in 630 g of aqueous ammonia (28° Be) through the incremental addition of 240 g of sodium hydroxide pellets. the feed of sodium hydroxide continues over a period of approximately one hour and fifty minutes. The reactants are allowed to remain undisturbed for a period of time. The reaction is terminated with withdrawal of unreacted magnesium, leaving a monomeric complex having a specific gravity of 1.264.

To prepare the magnesium-containing bleach, 50 ml of this magnesium-containing monomeric complex are reacted with 8 ml of hydrogen peroxide (50%) by thoroughly mixing the reactants until the magnesium-containing bleach crystallizes. The reaction was exothermic. The hydroperoxy group content of the bleach is found to be approximately 13.8%.

EXAMPLE 8

To produce a zinc-sodium-containing monomeric complex, 2,080 g of powdered zinc metal are reacted with 840 g of aqueous ammonia (28° Be) through the incremental addition of 320 g of sodium hydroxide pellets. The sodium hydroxide pellets are fed into the reaction system over a period of approximately two hours and ten minutes. The reactants are allowed to remain undisturbed for a period of time. The reaction is terminated by withdrawing the unreacted zinc metal, the monomeric complex having a specific gravity of 1.277.

To prepare the zinc-containing bleach, 50 ml of the above monomeric complex are reacted with 4.5 ml of hydrogen peroxide (50%) by thoroughly mixing the reactants until the bleach crystallizes as a substantially dry solid. This reaction is exothermic. An analysis of the bleach indicates that the hydroperoxy group content is approximately 8.3%.

The foregoing examples have been presented in order to illustrate various embodiments of the present invention. It should be understood, however, that the method and product of the present invention can not be limited thereto and modifications within the foregoing examples and description can be made while still falling within the spirit of the present invention. For example, it is possible to employ a mixture of inorganic monomeric complexes to achieve a bleach product having desired unique characteristics. Likewise, while the previous discussion has been centered around the preparation of inorganic monomeric complexes by a procedure set forth in applicant's co-pending application Ser. No. 631,949, filed on Nov. 17, 1975, the inorganic monomeric complex need not be produced by such process, as long as the metallic backbone is present and the reactive $NH_2$ groups are present for replacement by or chemical combination with the source of hydroperoxy groups. Accordingly, the present invention can not under any circumstances be limited to the exemplification previously made, but rather, must be construed to embrace any and all equivalents thereof.

What is claimed is:

1. A method of preparing an oxygen-containing bleach which comprises:

mixing at a temperature below about 75° F.

(a) an aqueous solution of a water-soluble, multimetal, inorganic, $NH_2$ group-containing monomeric complex; and (b) hydrogen peroxide whereby said hydrogen peroxide (b) reacts with said monomeric complex (a) upon mixing, and said oxygen-containing bleach crystallizes out of the reaction system.

2. The method of claim 1 wherein the water content of the reaction system produces said oxygen-containing bleach as a substantially dry solid.

3. The method of claim 1 wherein said monomeric complex includes at least one alkali metal and at least one non-alkaline metal of Groups I–VIII of the Periodic Table.

4. The method of claim 3 wherein said non-alkaline metal is selected from aluminum, magnesium, silicon, zinc, titanium, zirconium, molybdenum and tungsten.

5. The method of claim 3 wherein said alkali metal is selected from sodium and potassium.

6. The method of claim 1 wherein the reaction is maintained at about 75° F. or below through cooling.

7. The method of claim 1 wherein the reactants (a) and (b) are mixed at a molar ratio of about 1 to about 5 moles of hydrogen peroxide per mole of monomeric complex.

8. The method of claim 1 further including heating the oxygen-containing bleach to a temperature up to 160° F. to dry said oxygen-containing bleach.

9. An oxygen-containing bleach prepared by the method of claim 1.

* * * * *